(12) United States Patent
Schiffrin et al.

(10) Patent No.: US 7,964,384 B2
(45) Date of Patent: *Jun. 21, 2011

(54) ENDOTOXIN BINDING BY LACTIC ACID BACTERIA AND BIFIDOBACTERIA

(75) Inventors: Eduardo Schiffrin, Crissier (CH); Guillermo Kociubinski, West Hartford, CT (US)

(73) Assignee: Nestec S.A., Vevey (CH)

( * ) Notice: Subject to any disclaimer, the term of this patent is extended or adjusted under 35 U.S.C. 154(b) by 61 days.

This patent is subject to a terminal disclaimer.

(21) Appl. No.: 12/488,293

(22) Filed: Jun. 19, 2009

(65) Prior Publication Data

US 2010/0136662 A1 Jun. 3, 2010

Related U.S. Application Data

(62) Division of application No. 10/470,807, filed as application No. PCT/EP02/01163 on Feb. 1, 2002, now Pat. No. 7,550,285.

(30) Foreign Application Priority Data

Feb. 6, 2001 (EP) ..................... 0120043

(51) Int. Cl.
  *C12N 1/20* (2006.01)
  *A01N 25/02* (2006.01)
  *A01N 63/00* (2006.01)
  *A01N 65/00* (2006.01)
  *A01N 25/12* (2006.01)

(52) U.S. Cl. .................. 435/252.1; 435/252.9; 435/853; 435/854; 424/93.1; 424/93.45; 424/404

(58) Field of Classification Search .............. 435/252.1, 435/252.9, 853, 854; 424/93.1, 93.45, 404
See application file for complete search history.

(56) References Cited

U.S. PATENT DOCUMENTS

| 5,413,785 | A | 5/1995 | Nanji |
| 6,479,051 | B1 | 11/2002 | Bruce et al. |
| 6,506,389 | B2 | 1/2003 | Leer et al. |
| 6,827,953 | B1 | 12/2004 | Mizutani et al. |
| 7,550,285 | B2 * | 6/2009 | Schiffrin et al. ........... 435/252.9 |

FOREIGN PATENT DOCUMENTS

| EP | 0 555 618 | 8/1993 |
| WO | 99/59413 | 11/1999 |

OTHER PUBLICATIONS

Scardovi et al., 1974. Bifidobacterium animalis (Mitsuoka) comb. nov. and the "minimum" and "subtile" Groups of New Bifidobacteria Found in Sewage. International Journal of Systematic Bacteriology, vol. 24, No. 1, pp. 21-28.*
Scardovi et al., 1971. Starch Gel Electrophoresis of Fructose-6-Phosphate Phosphoketolase in the Genus Bifidobacterium. Journal of Bacteriology, vol. 106, No. 3, pp. 1036-1039.*
A. T.C.C. Catalogue, http://atcc.org/common catalog printed Dec. 23, 2007, pp. 1-2.
Hensyl, W.R. and Oldham, J.O. (Editors) Stedman's Medical Dictionary. 24th Edition. 1982. Williams and Wilkins, Baltimore, p. 121, col. 1, Lines 44-48; p. 755, col. 2, Lines 29-50.
Kasper, H. Protection Against Gastrointestinal Diseases- Presents Facts and Future Development. 1998. International Journal of Food Microbiology, vol. 41, pp. 127-131.
Perez et al., 1998. Applied and environmental Microbiology, vol. 64, pp. 21-26.

* cited by examiner

*Primary Examiner* — Jon P Weber
*Assistant Examiner* — Kailash Srivastava
(74) *Attorney, Agent, or Firm* — K&L Gates LLP

(57) ABSTRACT

The invention relates to the use of at least one strain of lactic acid bacteria and/or bifidobacteria having hydrophobic surface properties, for the preparation of a composition intended for the prevention or the treatment of endotoxin mediated and/or associated disorders and human or pet food compositions prepared thereof.

3 Claims, 5 Drawing Sheets

ENDOTOXIN BINDING BY LACTIC ACID BACTERIA AND BIFIDOBACTERIA

CROSS REFERENCE TO RELATED APPLICATIONS

Figure 1:
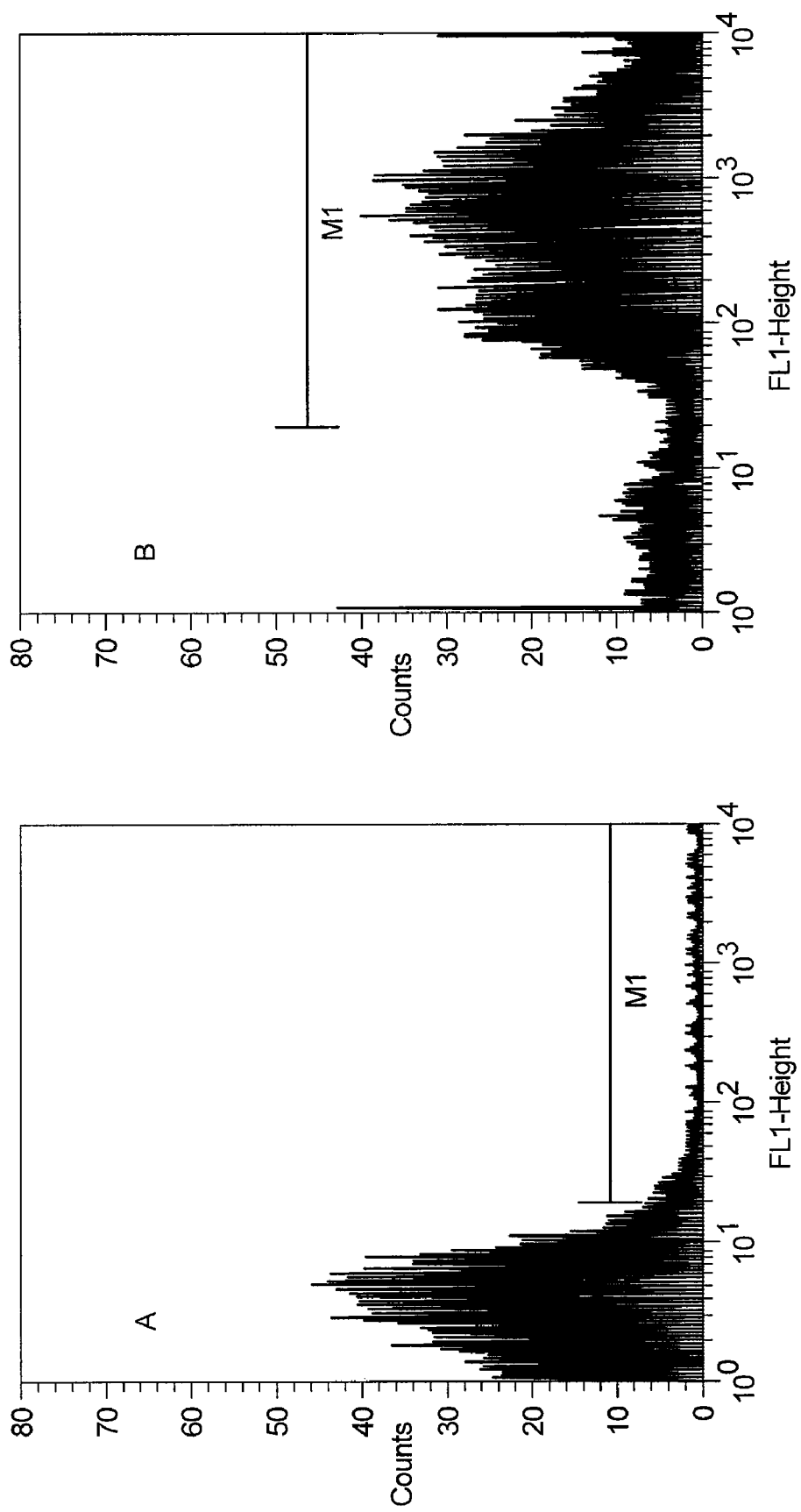

This application is a divisional of U.S. application Ser. No. 10/470,807, filed Feb. 19, 2004, now U.S. Pat. No. 7,550,285, which is a national stage designation of International Application No. PCT/EP02/01163, filed Feb. 1, 2002, which claims priority to European Application No. 0120043.2, filed Feb. 6, 2001, the entire contents of which are expressly incorporated herein by reference thereto.

The present invention relates to the use of lactic acid bacteria and/or bifidobacteria that are hydrophobic for the preparation of a food composition intended for the prevention or the treatment of endotoxin mediated and/or associated disorders. The invention also relates to composition prepared thereof.

BACKGROUND OF THE INVENTION

Sepsis-inducing toxins have been found associated with pathogenic bacteria, viruses, plants and venom. Among the well-described bacterial toxins are the endotoxins or lipopolysaccharides (LPS) of the gram-negative bacteria. These molecules are glycolipids that are ubiquitous in the outer membrane of all gram-negative bacteria, which are believed responsible for gram-negative sepsis. This type of sepsis is an extremely common condition and is often fatal.

A number of approaches for treating sepsis have been attempted. These include use of antibodies to LPS, use of antibodies to tumour necrosis factor, use of a soluble TNF receptor, use of a soluble interleukin-1 (IL-1) receptor, to name a few. While each approach has some efficacy, the overall results have been disappointing.

Others have attempted to design and study proteins which bind LPS/endotoxin, and illustrative reports of these attempts appear in Rustici, A. et al. Science (1993) 259:361-364; Matsuzaki, K. et al. Biochemistry (1993) 32:11704-11710; Hoess, A. et al. EMBO J (1993) 12:3351-3356; and Elsbach, P. et al. Current Opinion in Immunology (1993) 5:103-107. In fact, upon introduction of LPS into the blood, it may bind to a protein termed lipopolysaccharide-binding protein (LBP). Inhibition of LBP, e.g., with an anti-LBP antibody, has been suggested as therapeutically useful for treating endotoxin-mediated sepsis (International Patent Application No. PCT/US90/04250, filed Jul. 30, 1990). Also, work from several laboratories has shown that plasma lipoproteins, particularly high-density lipoproteins (HDL), bind and neutralise LPS (Skarnes et al., 1968, J. Bacteriology 95:2031; Flegel et al., 1993, Infect. Immunol. 61(12):5140) and that these particles may constitute the LPS-neutralising activity in plasma.

Previous treatments for endotoxin mediated and/or associated diseases has been retrospective (i.e., after development of clinical illness) and has been limited to chemotherapeutic intervention. Prevention measures were not achieved with such treatments.

Thus, there is a need in the art for an effective agent for neutralising gram-negative endotoxin (i.e., LPS), in order to prevent or alleviate symptoms of sepsis and septic shock.

The hydrophobic lactic acid bacteria and bifidobacteria of the present invention provide additional compounds which are capable of binding endotoxins and ameliorating/preventing its effects.

SUMMARY OF THE INVENTION

Thus, the present invention relates to the use of at least one strain of lactic acid bacteria and/or bifidobacteria that has hydrophobic surface properties, for the preparation of a composition intended for the prevention or the treatment of endotoxin mediated and/or associated disorders.

In fact, it has been surprisingly found that some lactic acid bacteria and bifidobacteria, particularly those with hydrophobic surface, have the ability to bind endotoxins. Thus, allowing their use as efficient agents for prevention of endotoxic shock and sepsis of gut origin, bacterial translocation, necrotising enterocolitis, inflammatory bowel disease, intestinal infections, chronic endotoxemia associated or promoting catabolic and systemic inflammation.

Preferably, the hydrophobic lactic acid bacteria or bifidobacteria has a percent hydrophobicity (% H) of at least 80, and more preferably from 85 to 100% H.

In a preferred embodiment, the strain is selected from the group consisting of *Lactobacillus johnsonii*, *Lactobacillus reuterii*, *Lactobacillus paracasei*, *Lactobacillus animalis*, *Lactobacillus ruminis*, *Lactobacillus acidophilus*, *Lactobacillus rahmnosus*, *Lactobacillus fermentum*, *Lactobacillus delbrueckii* subs. *lactis*, *Bifidobacterium* spp., *Bifidobacterium bifidum*, *Bifidobacterium longum*, *Bifidobacterium pseudolongum*, *Bifidobacterium infantis*, *Bifidobacterium adolescentis*.

In another aspect, the invention relates to an isolated strain of lactic acid bacteria or bifidobacteria having hydrophobic surface properties, that has been selected for its ability to bind endotoxins or co-aggregate with gram-negative bacteria.

In a further aspect, the invention provides a human or pet food composition for preventing or treating endotoxin mediated and/or associated disorders, which contains at least a strain of lactic acid bacteria and/or bifidobacteria having the above traits, associated with an ingestible support or a pharmaceutical matrix.

This composition presents the advantage to decrease small bowel bacterial overgrowth and diminish the endotoxin leakage from the gut to the internal milieu, a frequent disorder found in pets that may cause episodes of diarrhoea, malnutrition and intestinal and systemic inflammation, for example.

In a last aspect, the invention relates to a method of preventing or treating endotoxin mediated and/or associated disorders, comprising the step of feeding a human or animal a composition which contains at least a strain of lactic acid bacteria and/or bifidobacteria that has hydrophobic surface properties, associated with an ingestible support or a pharmaceutical matrix

DETAILED DESCRIPTION OF THE INVENTION

Within the following description, "NCC" designates Nestlé Culture Collection (Nestlé Research Centre, Verschez-les-Blanc, Lausanne, Switzerland).

With respect to the first object of the present invention, the use of at least one strain of lactic acid bacteria and/or bifidobacteria that has hydrophobic surface properties, for the preparation of a composition intended for the prevention or the treatment of endotoxin mediated and/or associated disorders, is concerned.

In fact, it has been surprisingly found that some lactic acid bacteria and bifidobacteria, particularly those with hydrophobic surface, have the ability to bind endotoxins.

Indeed, the bacterial strain according to the invention has the ability to bind endotoxins on the hydrophobic cell wall and therefore scavenge this proinflammatory product of gram negative bacteria that otherwise may translocate from the lumen of the gut into the blood and thereby trigger inflammatory reactions and, in very serious cases, endotoxic shock.

The lactic acid bacteria or bifidobacteria according to the invention have been selected among strains suitable for animal consumption, with regard to their percent hydrophobicity (% H), as described in A. G. Zavaglia et al., *Journal of Food protection*, Vol. 61, No. 7, 1998, p. 865-873.

Preferably, the bacterial strain according to the invention has a % H of at least 80, and more preferably from 85 to 100% H.

The determination of surface hydrophobicity was done by using the MATH method as previously described (Pérez, P. F. et al., 1998, *Appl. Environ. Microbiol.* 64: 21-26). Briefly, 2 ml of bacterial suspension (around $10^8$ CFU/ml, PBS) were extracted with 0.4 ml of xylene by vortexing them during 120 s. The phases were allowed to separate by decantation and $A_{600}$ of the aqueous phase was measured. Cell surface hydrophobicity (% H) was calculated with the formula H %=$[(A_0-A)/A_0] \times 100$ where $A_0$ and A are absorbances before and after extraction with xylene respectively.

In a preferred embodiment the bacterial strain may be selected from the group consisting of *Lactobacillus johnsonii, Lactobacillus reuterii, Lactobacillus paracasei, Lactobacillus animalis, Lactobacillus ruminis, Lactobacillus acidophilus, Lactobacillus rahmnosus, Lactobacillus fermentum, Lactobacillus delbrueckii* subs. *lactis Bifidobacterium* spp., *Bifidobacterium bifidum, Bifidobacterium longum, Bifidobacterium pseudolongum, Bifidobacterium infantis, Bifidobacterium adolescentis.*

In a most preferred embodiment the strain may be *Lactobacillus acidophilus* NCC 2463 (CNCM-I 2623), *Bifidobacterium bifidum* NCC 189 (previously CIDCA 536, CNCM-I-2333), *Bifidobacterium bifidum* NCC 235 (previously CIDCA 533, CNCM-I-2335), *Bifidobacterium adolescentis* NCC 251 (CNCM 1-2168), *Bifidobacterium lactis* (ATCC27536), for example.

Among the various strains selected in accordance with the present invention, the following strains were deposited by way of example under the Budapest Treaty at the Collection Nationale de Cultures de Microorganismes (CNCM), Institut Pasteur, 28 rue du Docteur Roux, 75724 Paris Cedex 15, France, *Lactobacillus acidophilus* NCC 2463 on the 2 Feb. 2001 under the reference CNCM I-2623, and *Bifidobacterium bifidum* NCC 189 and NCC 235 on the 12 Oct. 1999 under the references CNCM-I-2333 and CNCM 1-2335, respectively. *Bifidobacterium adolescentis* NCC 251 was deposited on the 15 Mar. 1999 under the reference CNCM I-2168.

The strain of *Bifidobacterium lactis* (Bb12) (ATCC27536) is provided by Hansen (Chr. Hansen A/S, 10-12 Boege Alle, P.O. Box 407, DK-2970 Hoersholm, Danemark). It has a hydrophobicity of 89% H.

The bacterial strain according to the present invention may be used for the preparation of compositions intended for improving human or animal health, particularly for the prevention or treatment of disorders related to endotoxins in humans and pets. The bacterial strain may be used as efficient agent for prevention of endotoxic shock and sepsis of gut origin, bacterial translocation, necrotising enterocolitis, inflammatory bowel disease, intestinal infections, and chronic endotoxemia associated or promoting catabolic and systemic inflammation, for example.

The bacterial strain according to the invention may be used in its viable or inactivated form.

In a preferred embodiment the lactic bacteria strain is used in the presence of its fermented growth medium. The said medium can be either sterilised alone or with a food, extruded or spray-dried, chilled or shelf stable, for example.

The bacterial strain may be used so that the amount available for the individual may correspond to about $10^3$-$10^{14}$ cfu per day. This amount depends on the individual weight, and it is preferably of about $10^9$-$10^{12}$ cfu/day for humans and $10^7$-$10^{10}$ cfu/day for pets.

According to another aspect, the present invention relates to an isolated strain of lactic acid bacteria or bifidobacteria having hydrophobic surface properties and having the ability to bind endotoxins or co-aggregate with gram-negative bacteria.

The ability of the bacterial strain according to the present invention to bind endotoxins can be measured easily using FITC-labelled endotoxins, measuring the association of radiolabelled endotoxin to bacterial cells, in this case the molecular structure of the endotoxin is unaltered as compared with the possible modifications that may suffer the molecule after conjugation with the FITC (see examples).

Preferably, the capacity of the bacterial strain to remove endotoxin from a solution that mimics the quantity of endotoxins found in the human intestine is measured. For example, levels of endotoxins were examined with the microassay for the detection of 2-keto-3-deoxyoctonate group in the lipopolysaccharide of gram-negative bacteria (Karkhanis Y D, et al., *Analytical Chemistry* (1978) 85: 595-601). Bacteria removing more that 30% of the endotxin content from these solutions were preferably selected. The non-hydrophobic bacteria tested in this assay were unable to modify the initial content of endotoxin (see examples).

Such bacterial strain may be used as described above, and particularly as efficient agent for prevention of endotoxic shock and sepsis of gut origin, bacterial translocation, necrotising enterocolitis, inflammatory bowel disease, intestinal infections, chronic endotoxemia associated or promoting catabolic and systemic inflammation, for example.

According to a further aspect, the present invention relates to a human or pet food composition containing at least an isolated strain of lactic acid bacteria and/or bifidobacteria, said strain having the above traits, associated with an ingestible support or a pharmaceutical matrix.

The strain may be selected as described above.

Preferably, the lactic acid bacteria or bifidobacteria may be administered as a supplement to the normal diet or as a component of a nutritionally complete human or pet food.

The human or pet food composition may comprise at least the lactic acid bacteria and/or bifidobacteria strain, as described above, so that the amount available for the individual may correspond to about $10^3$-$10^{14}$ cfu per day. This amount depends on the individual weight, and it is preferably of about $10^9$-$10^{12}$ cfu/day for humans and $10^7$-$10^{10}$ cfu/day for pets.

The human food may be in the form of a nutritional formula, an infant formula, milk-based products, dairy products, cereal-based products, for example. To prepare such a food product or composition, the bacterial strain as described above can be incorporated into a food, such as cereal powder, milk powder, a yoghurt, during its manufacture, for example.

In one embodiment, a nutritional formula comprising a source of protein and at least one bacterial strain according to the invention can be prepared. Dietary proteins are preferably used as a source of protein. The dietary proteins may be any suitable dietary protein; for example animal proteins (such as milk proteins, meat proteins and egg proteins), vegetable proteins (such as soy, wheat, rice or pea proteins), mixtures of free amino acids, or combination thereof Milk proteins such as casein, whey proteins and soy proteins are particularly preferred. The composition may also contain a source of carbohydrates and a source of fat.

If the nutritional formula includes a fat source, the fat source preferably provides about 5% to about 55% of the energy of the nutritional formula; for example about 20% to about 50% of the energy. The lipids making up the fat source may be any suitable fat or fat mixtures. Vegetable fats are particularly suitable; for example soy oil, palm oil, coconut oil, safflower oil, sunflower oil, corn oil, canola oil, lecithin, and the like. Animal fats such as milk fats may also be added if desired.

If the nutritional formula includes a carbohydrate source, the carbohydrate source preferably provides about 40% to about 80% of the energy of the nutritional formula. Any suitable carbohydrates may be used, for example sucrose, lactose, glucose, fructose, corn syrup solids, and maltodextrins, and mixtures thereof.

Dietary fibre may also be added if desired. Numerous types of dietary fibre are available. Suitable sources of dietary fibre, among others, may include soy, pea, oat, pectin, guar gum, and gum arabic. If used, the dietary fibre preferably comprises up to about 5% of the energy of the nutritional formula. Suitable vitamins and minerals may be included in the nutritional formula in the usual manner to meet the appropriate guidelines. One or more food grade emulsifiers may be incorporated into the nutritional formula if desired; for example diacetyl tartaric acid esters of mono-diglycerides, lecithin and mono- and di-glycerides. Similarly suitable salts and stabilisers may be included.

The nutritional formula is preferably enterally administrable; for example in the form of a powder, a liquid concentrate, or a ready-to-drink beverage.

The nutritional formula may be prepared in any suitable manner. For example, the nutritional formula may be prepared by blending together the source of dietary protein, the carbohydrate source, and the fat source in appropriate proportions. If used, the emulsifiers may be included in the blend. The vitamins and minerals may be added at this point but are usually added later to avoid thermal degradation. Any lipophilic vitamins, emulsifiers and the like may be dissolved into the fat source prior to blending. Water, preferably water that has been subjected to reverse osmosis, may then be mixed in to form a liquid mixture. The temperature of the water is conveniently about 50° C. to about 80° C. to aid dispersal of the ingredients. Commercially available liquefiers may be used to form the liquid mixture. The liquid mixture is then homogenised; for example in two stages.

The liquid mixture may then be thermally treated to reduce bacterial loads. For example, the liquid mixture may be rapidly heated to a temperature in the range of about 80° C. to about 150° C. for about 5 seconds to about 5 minutes. This may be carried out by steam injection, autoclave or by heat exchanger; for example a plate heat exchanger. The liquid mixture may then be cooled to about 60° C. to about 85° C.; for example by flash cooling. The liquid mixture may then be again homogenised; for example in two stages at about 7 MPa to about 40 MPa in the first stage and about 2 MPa to about 14 MPa in the second stage. The homogenised mixture may then be further cooled to add any heat sensitive components; such as vitamins and minerals. The pH and solids content of the homogenised mixture is conveniently standardised at this point.

If it is desired to produce a powdered nutritional formula, the homogenised mixture is transferred to a suitable drying apparatus such as a spray drier or freeze drier and converted to powder. The powder should have a moisture content of less than about 5% by weight.

If it is desired to produce a liquid formula, the homogenised mixture is preferably aseptically filled into suitable containers. Aseptic filling of the containers may be carried out by pre-heating the homogenised mixture (for example to about 75 to 85° C.) and then injecting steam into the homogenised mixture to raise the temperature to about 140 to 160° C.; for example at about 150° C. The homogenised mixture may then be cooled, for example by flash cooling, to a temperature of about 75 to 85° C. The homogenised mixture may then be homogenised, further cooled to about room temperature and filled into containers. Suitable apparatus for carrying out aseptic filling of this nature is commercially available. The liquid formula may be in the form of a ready to feed formula having a solids content of about 10 to about 14% by weight or may be in the form of a concentrate; usually of solids content of about 20 to about 26% by weight. Flavours may be added to the liquid formulas so that the formulas are provided in the form of convenient, flavoursome, ready-to-drink beverages.

In an another embodiment, a usual food product may be enriched with the bacterial strain according to the present invention. For example, a fermented milk, yoghurt, a fresh cheese, a renneted milk, a confectionery bar, breakfast cereal flakes or bars, drinks, milk powders, soy-based products, non-milk fermented products or nutritional supplements for clinical nutrition.

In a further embodiment, a nutritionally complete pet food composition can be prepared. It may be in powdered, dried form, semi-moist or a wet, chilled or shelf stable pet food product. It can also be dietary supplements for pets or pharmaceutical compositions. These pet foods may be produced as is conventional. Apart from the bacteria strain, these pet foods may include any one or more of a starch source, a protein source and lipid source.

Suitable starch sources are, for example, grains and legumes such as corn, rice, wheat, barley, oats, soy, and mixtures of these. Suitable protein sources may be selected from any suitable animal or vegetable protein source; for example meat and meal, poultry meal, fish meal, soy protein concentrates, milk proteins, gluten, and the like. For elderly animals, it is preferred for the protein source to contain a high quality protein. Suitable lipid sources include meats, animal fats and vegetable fats. Further, various other ingredients, for example, sugar, salt, spices, seasonings, vitamins, minerals, flavouring agents, fats and the like may also be incorporated into the pet food as desired.

For dried pet foods a suitable process is extrusion cooking, although baking and other suitable processes may be used. When extrusion cooked, the dried pet food is usually provided in the form of a kibble. If a prebiotic is used, the prebiotic may be admixed with the other ingredients of the dried pet food prior to processing. A suitable process is described in European patent application No 0850569; the disclosure of which is incorporated by reference. If a probiotic micro-organism is used, the organism is best coated onto or filled into the dried pet food. A suitable process is described in European patent application No 0862863; the disclosure of which is incorporated by reference.

For wet foods, the processes described in U.S. Pat. Nos. 4,781,939 and 5,132,137 may be used to produce simulated meat products. The disclosures of these patents are incorporated by reference. Other procedures for producing chunk type products may also be used; for example cooking in a steam oven. Alternatively, loaf type products may be produced by emulsifying a suitable meat material to produce a meat emulsion, adding a suitable gelling agent, and heating the meat emulsion prior to filling into cans or other containers.

The amount of prebiotic in the pet food is preferably about 20% by weight; especially about 10% by weight. For example, the prebiotic may comprise about 0.1% to about 5% by weight of the pet food. For pet foods which use chicory as the prebiotic, the chicory may be included to comprise about 0.5% to about 10% by weight of the feed mixture; more preferably about 1% to about 5% by weight.

If a probiotic microorganism is used, the pet food preferably contains about $10^4$ to about $10^{10}$ cells of the probiotic microorganism per gram of the pet food; more preferably about $10^6$ to about $10^8$ cells of the probiotic microorganism per gram. The pet food may contain about 0.5% to about 20% by weight of the mixture of the probiotic microorganism; preferably about 1% to about 6% by weight; for example about 3% to about 6% by weight.

The pet foods may contain other active agents such as long chain fatty acids. Suitable long chain fatty acids include alpha-linoleic acid, gamma linoleic acid, linoleic acid, eicosapentanoic acid, and docosahexanoic acid. Fish oils are a suitable source of eicosapentanoic acids and docosahexanoic acid. Borage oil, blackcurrent seed oil and evening primrose oil are suitable sources of gamma linoleic acid. Safflower oils, sunflower oils, corn oils and soybean oils are suitable sources of linoleic acid. If necessary, the pet foods are supplemented with minerals and vitamins so that they are nutritionally complete.

Further, if desired, the bacteria strain may be encapsulated; for example in a sugar matrix, fat matrix or polysaccharide matrix.

The amount of the pet food to be consumed by the pet to obtain a beneficial effect will depend upon the size or the pet, the type of pet, and age of the pet. However an amount of the pet food to provide a daily amount of about $10^3$-$10^{14}$ cfu of at least one lactic acid bacteria or bifidobacteria strain would usually be adequate. Preferably about $10^9$-$10^{10}$ cfu/day for dogs or $10^7$-$10^{10}$ cfu/day for cats are administered, for example.

The composition according to the invention is particularly intended for the prophylaxis or the treatment of infections related to gram negative bacteria, endotoxin producing bacteria such as *Helicobacter* spp, *Samonella* spp, and also to small intestinal bacterial overgrowth (SIBO) all of which may clinically manifest with diarrhoea, intestinal or systemic inflammatory conditions, or catabolism and malnutrition.

According to a last aspect, the invention provides a method of preventing or treating endotoxin mediated and/or associated disorders, comprising the step of feeding a human or animal a composition which contains at least a strain of lactic acid bacteria and/or bifidobacteria that has hydrophobic surface properties, associated with an ingestible support or a pharmaceutical matrix.

This method may be particularly intended for the prophylaxis or the treatment of infections related to gram negative bacteria, endotoxin producing bacteria such as *Helicobacter* spp, *Samonella* spp, and also to small intestinal bacterial overgrowth (SIBO) all of which may clinically manifest with diarrhoea, intestinal or systemic inflammatory conditions, or catabolism and malnutrition.

The following examples are given by way of illustration only and in no way should be construed as limiting the subject matter of the present application. All percentages are given by weight unless otherwise indicated. The examples are preceded by a brief description of the figures.

FIGURES

FIG. 1: Histogram plots for *Bifidobacterium bifidum* strain NCC 189 (previously CIDCA 536, CNCM I-2333) showing binding of FITC-LPS. A: control without FITC-LPS. B: incubation with 50 µl/ml FITC-LPS. At least 16000 events were analysed.

Figure 2:
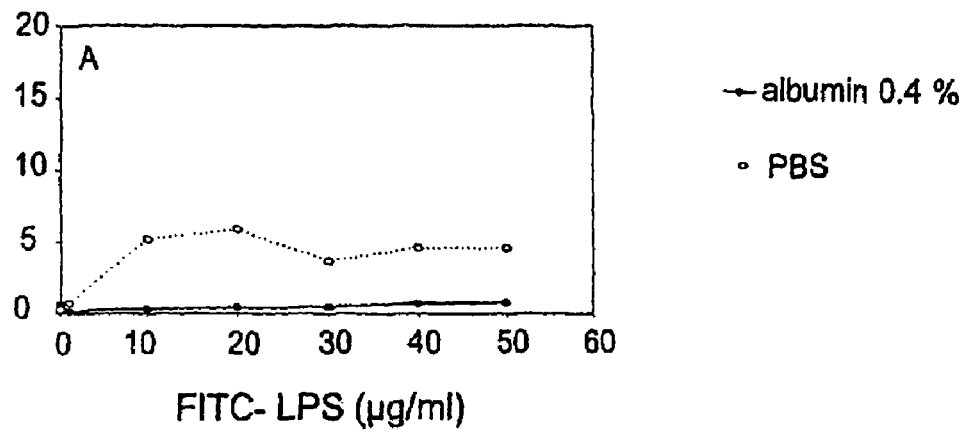
Figure 2:
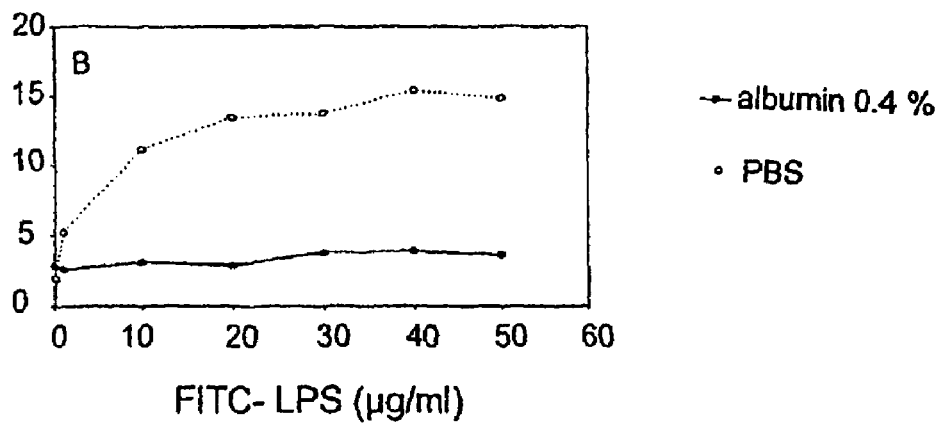
Figure 2:
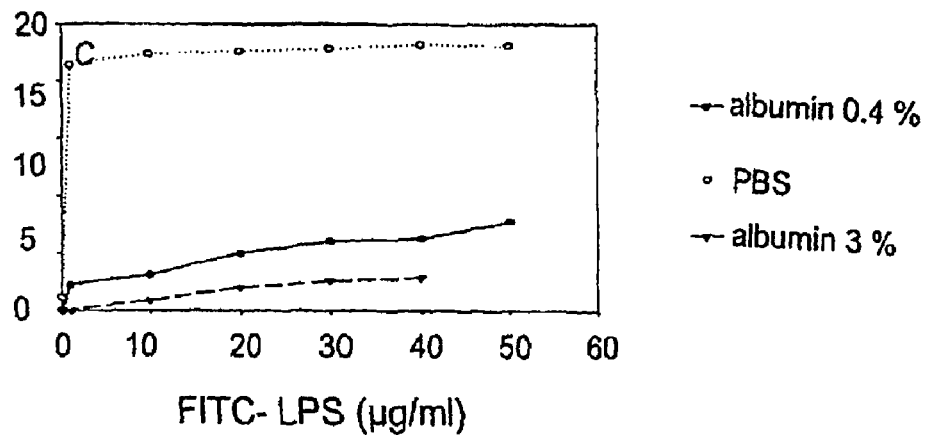

FIG. 2: Effect of albumin on FITC-LPS binding by lactic acid bacteria and bifidobacteria. A: *Bifidobacterium bifidum* strain NCC 200 (previously CIDCA 538, CNCM I-2334). B: *Lactobacillus acidophilus* strain NCC 2463 (CNCM I-2623). C: *Bifidobacterium bifidum* strain NCC 189 (previously CIDCA 536, CNCM I-2333).

Figure 3:
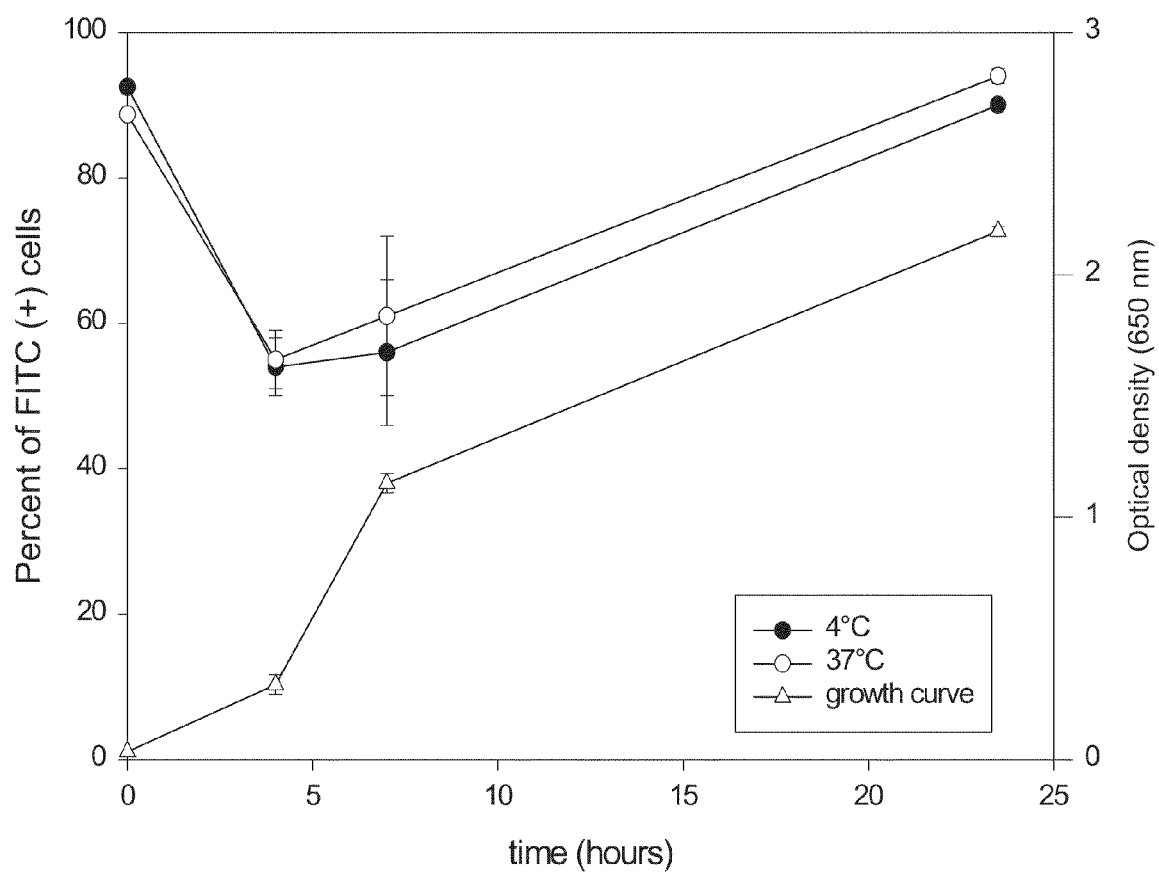

FIG. 3: Kinetics of growth and FITC-LPS binding for *Bifidobacterium bifidum* strain NCC 189 (previously CIDCA 536, CNCM 1-2333). Values are means from two independent experiments.

Figure 4:
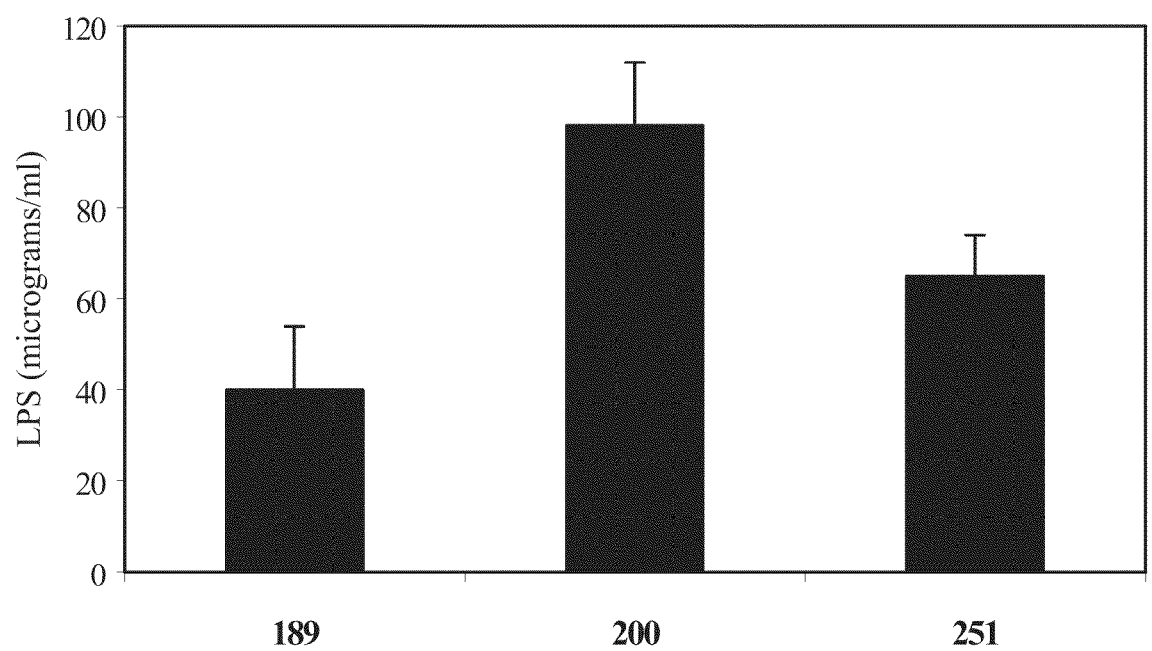

FIG. 4: Binding of LPS by *Bifidobacterium* strain, detected by the microassay to determine 2-keto-3-deoxyoctonato (KDO) in lipopolysaccharide. The initial concentration of the solution was 100 µg/ml. The bars show the final concentration after incubation of the solution with hydrophobic bifidobacterial strains NCC 189 and NCC 251 (CNCM I-2168) compared with a non-hydrophobic strain of bifidobacteria (NCC 200 (CNCM I-2334)).

Figure 5:
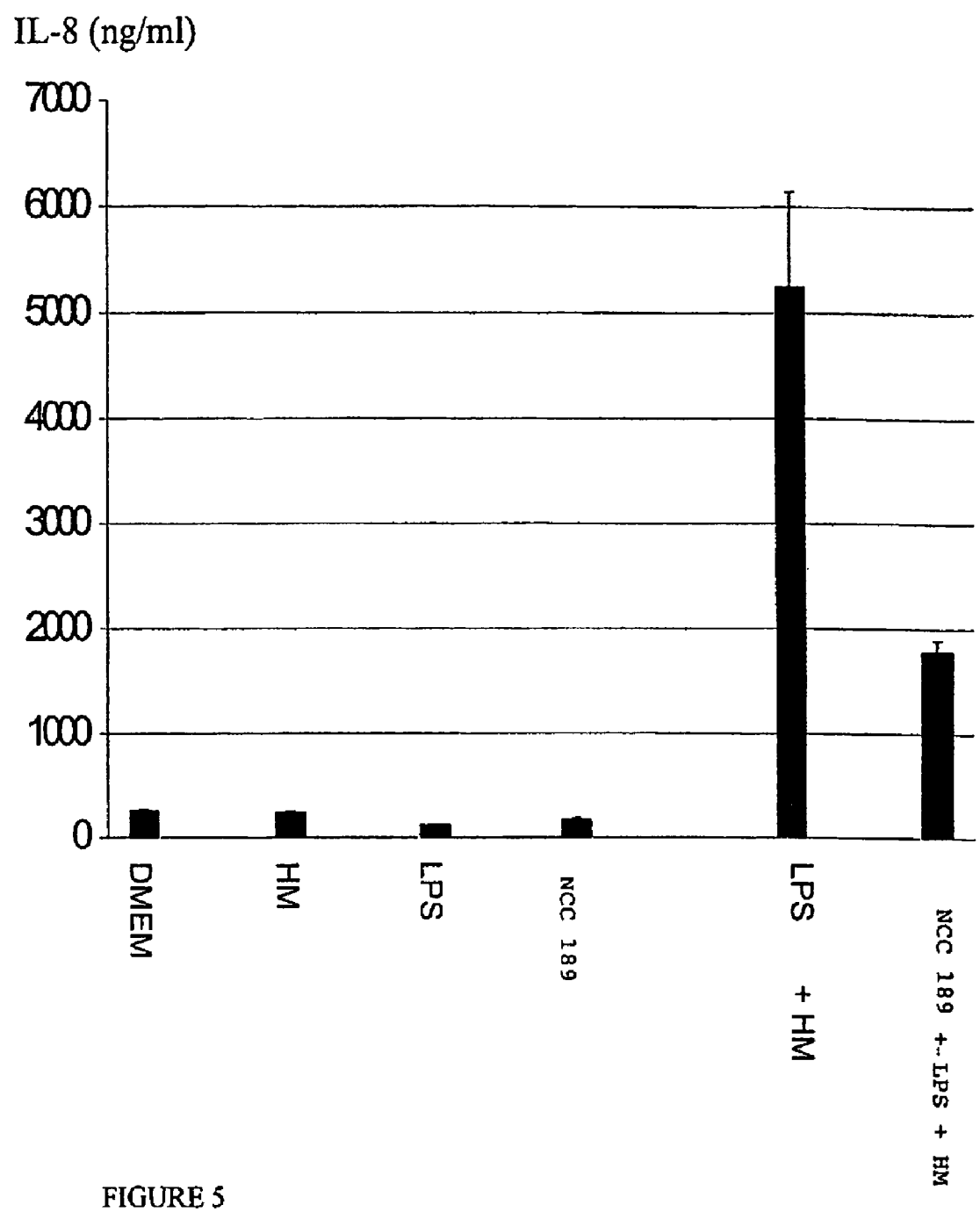

FIG. 5: Proinflammatory activity (IL-8 (ng/mL)) of LPS solution preincubated with hydrophobic bacteria on HT-29 human epithelial cells.

Control samples of DMEM, Human milk (HM) 2%, LPS (2.5 µg/ml) alone, *Bifidobacterium bifidum* strain NCC 189 (1.5e8 cfu/ml) alone were tested for background stimulatory activity. Test solutions of LPS+human milk (source of sCD14) were compared with solution containing LPS 2.5 µg/ml+HM 2% preincubated with *Bifidobacterium bifidum* strain NCC 189(1.5e8 cfu/ml).

EXAMPLES

Example 1

Selection of Hydrophobic Lactic Acid Bacteria Strain According to the Invention

The selection of hydrophobic bacteria was initially based in the % of partition of bacterial cells between an organic (hydrophobic) and an aqueous phase. Determination of surface hydrophobicity was done by using the MATH method as previously described (Pérez, P. F. et al., 1998, *Appl. Environ. Microbiol.* 64: 21-26). Briefly, 2 ml of bacterial suspension (around $10^8$ CFU/ml, PBS) were extracted with 0.4 ml of xylene by vortexing them during 120 s. The phases were allowed to separate by decantation and $A_{600}$ of the aqueous phase was measured. Cell surface hydrophobicity (% H) was calculated with the formula H $\%=[(A_0-A)/A_0]\times100$ where $A_0$ and A are absorbances before and after extraction with xylene respectively.

Subsequently lactic acid bacteria or bifidobacteria were selected by their capacity to remove endotoxin from a solution that mimics the quantity of endotoxin found in the human intestine. Levels of endotoxin were examined with the microassay for the detection of 2-keto-3-deoxyoctonate group in the lipopolisaccharide of gram-negative bacteria (Karkhanis Y D, et al., *Analytical Chemistry* (1978) 85:595-601).

Bacteria removing more that 30% of the endotoxin content from these solutions were selected. The non-hydrophobic bacteria tested in this assay were unable to modify the initial content of endotoxin.

Example 2

In-Vitro Effect of Lactic Acid Bacteria as Endotoxin Scavenger

The interaction between LPS from *Escherichia coli* and lactic acid bacteria bearing different surface properties was studied having selected bacteria with more of 80% H and some non-hydrophobic "negative" controls the interaction with fluorescent labelled endotoxin was performed with flow cytometry.

Materials and Methods
Bacterial Strains and Growth Conditions

Strain *Lactobacillus acidophilus* NCC 2463 (CNCM I-2623) was from Nestec collection (Lausanne, Switzerland). Strains *Bifidobacterium bifidum* NCC 189 (previously CIDCA 536, I-2333) and *Bifidobacterium bifidum* NCC 200 (previously CIDCA 538, (CNCM I-2334)) were from the collection of the Centro de Investigacion y Desarrollo en Criotecnologia de Alimentos (La plata, Argentina). Frozen suspensions (−80° C.) preserved with 10% (vol./vol.) glycerol were reactivated once in MRS broth before experiments. All cultures were conducted at 37° C. in anaerobic conditions (BBL GasPak Plus).

FITC-LPS Binding

Lipopolysaccharide and FITC-labelled lypopolysaccharide were from *Escherichia coli* serotype 0111:B4 (Skelly, R. R et al., 1979, *Infect. Immun.* 23: 287-293) and were purchased by Sigma. Stock solutions containing 1000 µl/ml were prepared in distilled water and diluted appropriately.

Bacterial cultures were washed three times with PBS and suspensions were standardised to $10^7$ CFU/ml. 400 µl were mixed with different amounts of FITC-LPS or LPS to obtain concentrations ranging from 0 to 50 µg/ml in the reaction mixture. Incubations were performed at 4° C. or 37° C. during 30 minutes and then, cells were washed two times with PBS and fixed with paraformaldehyde 1% (vol./vol.) during 30 minutes at 4° C. Flow cytometric analysis was done using a blue-green excitation light (FACScan™).

Surface Hydrophobicity

Determination of surface hydrophobicity was done by using the MATH method as previously described (Pérez, P. F. et al., 1998, *Appl. Environ. Microbiol.* 64: 21-26). Briefly, 2 ml of bacterial suspension (around $10^8$ CFU/ml, PBS) were extracted with 0.4 ml of xylene by vortexing them during 120 s. The phases were allowed to separate by decantation and $A_{600}$ of the aqueous phase was measured. Cell surface hydrophobicity (% H) was calculated with the formula $H\% = [(A_0 - A)/A_0] \times 100$ where $A_0$ and A are absorbances before and after extraction with xylene respectively.

Results

Surface hydrophobicities of strains under study are shown in Table 1. Values were 93 and 96% for strains *Lactobacillus acidophilus* NCC 2463 (CNCM I-2623) and *Bifidobacterium bifidum* NCC 189 (CNCM I-2333) respectively whereas strain *Bifidobacterium infantis* NCC 200 (CNCM I-2334) was not hydrophobic and showed values around 3%.

TABLE 1

Hydrophobicities of strains under study. Values are means of at least 3 determinations.

| Strain | Hydrophobicity % |
|---|---|
| NCC 2463 (CNCM I-2623) | 93 ± 3 |
| NCC 189 (CNCM I-2333) | 96 ± 3 |
| NCC 200 (CNCM I-2334) | 3 ± 2 |

Incubation of strain NCC 189 with 50 µg/ml of FITC-labelled LPS clearly shifts bacterial population into a fluorescent zone. Events situated in the right side of the graph (marker M1) represents 90% of the gated population (FIG. 1B). For suspensions incubated without FITC-LPS, only 2% of the events are situated in different binding capability.

Table 2 (below) shows that FITC-LPS binding is dose dependent. 5 and 15% of FITC (+) cells were found for strains NCC200. On the other hand, strain NCC 189 shows around 95% of FITC (+) cells. Saturation occurs around 10 µg/ml of FITC-LPS. Addition of albumin, a lipid binder, clearly reduces FITC (+) ratio in all strains under study (FIG. 2). However, strain CIDCA 536 shows around 30% of FITC (+) cells in the presence of 0.4% albumin and 50 µg/ml of FITC-LPS (FIG. 2C). Furthermore for this strain, 10% of FITC (+) cells were found with albumin concentrations as high as 3%. Divalent cations (Ca2+0.9 mM and Mg2+0.5 mM) did not modified binding (data not shown).

TABLE 2

Percent of FITC (+) bacteria at different concentrations of FITC-LPS. At least 30000 events were analysed.

| FITC-LPS | Strain | |
|---|---|---|
| (µg/ml) | NCC 189 | NCC 200 |
| 0 | 0.1 | 0.2 |
| 1 | 88.1 | 0.7 |
| 10 | 92.1 | 5.2 |
| 20 | 92.8 | 5.9 |
| 30 | 93.9 | 3.7 |
| 40 | 94.7 | 4.6 |
| 50 | 94.8 | 4.6 |

Binding of FITC-LPS for *Bifidobacterium bifidum* strain NCC 189 (previously CIDCA 536, CNCM I-2333) was strongly dependent on growth phase (FIG. 3). Bacteria harvested in stationary phase shows a high ratio of FITC (+) cells. These values fall dramatically during lag phase and were progressively restored during growth. No differences between binding at 4° C. and 37° C. were found.

In summary, highly hydrophobic strains show FITC (+) cells that reach around 95% for strain NCC 189. Non hydrophobic strain NCC 200 never reaches values higher than 5%. These results show that binding of LPS correlates with surface hydrophobicity.

These results clearly indicated that hydrophobic bacteria bind FITC-labelled endotoxin and thereby become fluorescent. At a concentration of 10 µg/ml of endotoxin more than 90% of the hydrophobic cell cultures become fluorescent as detected with flow cytometry; in contrast, less than 10% of non-hydrophobic bacterial cells became positive under similar endotoxin concentrations.

When hydrophobic cultures were introduced in media containing endotoxin at concentration ranging between 30 and 90 µg/ml, bacterial cultures at concentration of $10^7$ to $10^8$ bacterial per ml removed at least 20% of the present endotoxin. This data was confirmed using radiolabelled endotoxin.

Example 3

Experiments on Human Immunocompetent Cells

The abrogation of the pro-inflammatory reaction in human immunocompetent cells induced by endotoxin by the presence in the culture system of hydrophobic strains in comparison with non-hydrophobic bacteria was studied.

Hydrophobic *Bifidobacterium bifidum* NCC 189 (CNCM I-2333) and non-hydrophobic *Bifidobacterium infantis* NCC 200 (CNCM I-2334) were incubated in a solution containing a defined quantity of endotoxin as determined by the KDO method (see example 1) (FIG. 4).

Endotoxin presence after incubation with bacteria suspension was clearly diminished by the hydrophobic strain whereas no changes were observed for the non-hydrophobic strain.

Example 4

Functional Studies for Hydrophobic Bacteria

Materials and Methods

Washed bacteria were resuspended in DMEM-high glucose (AMIMED) and were preincubated with LPS of *Escherichia coli* O111: B4 (Sigma) at a final concentration of 2.5 µg/ml. After centrifugation 200 µl of supernatant or resuspended bacterial pellet were used to stimulate HT-29 epithelial cells.

After 20-h culture at 37° C. the HT-29 cell culture supernatant was examined for the presence of IL-8 using an ELISA technique.
Results.

The results are presented in FIG. 5. Proinflammatory activity of LPS is significantly reduced when an LPS solution is preincubated with hydrophobic bacteria. After centrifugation the supernatant added to a human epithelial cell culture (in the presence of human milk since LPS stimulation is dependent on sCD14 presence) is significantly reduced with respect to the supernatant that has not been preincubated with the hydrophobic bacteria.

Example 5

Infant Formula

To obtain an infant formula we prepare the following mixture containing for 100 ml of formula: 0.5 to 5%, preferably 2% of peptides, 0.2 to 10%, preferably 4% of fat, 1 to 25%, preferably 8% of non-levan carbohydrates (including lactose 65%, maltodextrin 20%, starch 15%), and at least $10^6$ cfu/ml of the following strains: *Lactobacillus acidophilus* NCC 2463 (CNCM I-2623), *Bifidobacterium bifidum* NCC189 (CNCM I-2333), *Bifidobacterium bifidum* CNCM I-2335, *Bidifobacterium adolescentis* CNCM I-2168, in combination with traces of vitamins and oligoelements to meet daily requirements, and 0.01 to 2%, preferably 0.3%, of minerals, and 50 to 90%, preferably 75% of water.

Example 6

Use of Hydrophobic Lactic Acid Bacteria According to the Invention in Dairy Products One or more strain of *Bifidobacterium bifidum* (CNCM I-2333), *Lactobacillus acidophillus* NCC 2463 (CNCM I-2623), *Bifidobacterium bifidum* NCC235 (CNCM I-2335) or *Bifidobacterium adolescentis* NCC251 (CNCM I-2168), according to the present invention may be used for the manufacture of fermented yoghurt-like milk products.

To do this, 1 l of a milk product containing 2.8% of fats and supplemented with 2% of skimmed milk powder and 6% of sucrose is prepared, it is pasteurised at 96° C. for 30 minutes and its temperature is then lowered to 42° C. Precultures of a non-thickening strain of *Streptococcus thermophilus* and of a non-viscous strain *Lactobacillus bulgaricus* are reactivated in a sterile MSK culture medium containing 10% of reconstituted milk powder and 0.1% of commercial yeast extract.

A preculture of one or more of the strain is also reactivated in a medium containing 10% of reconstituted milk powder and 0.1% of commercial yeast extract with 1% sucrose. The pasteurised milk product is then inoculated with 1% of each of these reactivated precultures and this milk product is then allowed to ferment at 32° C. until the pH reaches a value of 4.5. Fermented milks yoghurt-like products are produced in this way and stored at 4° C.

Example 7

Dry Dog Food

A feed mixture is made up of about 58% by weight corn, about 5.5% by weight of corn gluten, about 22% by weight of chicken meal, 2.5% dried chicory, fermented milk by strains of *Lactobacillus acidophilus* NCC 2463 (CNCM-I 2623)) so that the corresponding amount for the dog is about $10^9$-$10^{10}$ cfu/day, and salts, vitamins and minerals making up the remainder.

The fed mixture is fed into a preconditioner and moistened. The moistened feed is then fed into an extruder-cooker and gelatinised. The gelatinised matrix leaving the extruder is forced through a die and extruded. The extrudate is cut into pieces suitable for feeding to dogs, dried at about 110° C. for about 20 minutes, and cooled to form pellets.

This dry dog food is able to improve pet health, and particularly prevents disorders related to endotoxins in pets.

The invention claimed is:

1. An isolated biologically pure strain selected from the group consisting of *Lactobacillus acidophilus* NCC 2463 (CNCM-I 2623), *Bifidobacterium bifidum* NCC 189 (CNCM-I-2333), *Bifidobacterium bifidum* NCC 235 (CNCM-1-2335) and *Bifidobacterium adolescentis* NCC 251 (CNCM-I-2168) each having hydrophobic surface properties and an ability to bind endotoxins or co-aggregate with Gram negative bacteria.

2. The strain of claim 1, wherein the strain binds at least 30% of endotoxin from solutions where the concentrations are similar to an intestinal content of endotoxin.

3. The strain of claim 1, wherein the strain has a percent hydrophobicity of at least 80.

* * * * *